United States Patent [19]

Berg et al.

[11] 4,379,028

[45] Apr. 5, 1983

[54] SEPARATION OF ETHYL ACETATE FROM ETHANOL AND WATER BY EXTRACTIVE DISTILLATION

[76] Inventors: Lloyd Berg; Pisant Ratanapupech, both of 1314 S. Third Ave., Bozeman, Mont. 59715

[21] Appl. No.: 363,638

[22] Filed: Mar. 30, 1982

[51] Int. Cl.³ .......................... B01D 3/40; C07C 67/48
[52] U.S. Cl. .................................... 203/51; 203/56; 203/57; 203/60; 203/64; 203/65; 560/248
[58] Field of Search ................... 203/57, 56, 60, 64, 203/14, 19, 51, 63, 65; 560/248

[56] References Cited

U.S. PATENT DOCUMENTS 3,689,372  9/1972  Sugano et al. ..................... 203/57

FOREIGN PATENT DOCUMENTS 1172677  6/1964  Fed. Rep. of Germany ........ 203/60

*Primary Examiner*—Wilbur L. Bascomb, Jr.

[57] ABSTRACT

Ethyl acetate cannot be completely removed from ethanol and water mixtures by distillation because of the presence of the minimum ternary azeotrope. Ethyl acetate can be readily removed from mixtures containing it, ethanol and water by using extractive distillation in which the extractive distillation agent is a higher boiling oxygenated of nitrogenous organic compound or a mixture of these. Typical examples of effective agents are: dimethylsulfoxide, glycerine and diethylene glycol, 1-naphthol, hydroquinone and N,N-dimethylformamide.

9 Claims, No Drawings

SEPARATION OF ETHYL ACETATE FROM ETHANOL AND WATER BY EXTRACTIVE DISTILLATION

FIELD OF THE INVENTION

This invention relates to a method for separating ethyl acetate from ethanol and water using certain higher boiling liquids as the extractive agent in extractive distillation.

DESCRIPTION OF PRIOR ART

Extractive distillation is the method of separating close boiling compounds or azeotropes by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. When the compounds to be separated normally form an azeotrope, the proper agents will cause them to boil separately during extractive distillation and thus make possible a separation in a rectification column that cannot be done at all when no agent is present. The extractive agent should boil higher than any of the close boiling liquids being separated and not form minimum boiling azeotropes with them. Usually the extractive agent is introduced a few plates from the top of the column in insure that none of the extractive agent is carried over with the lowest boiling component. This usually requires that the extractive agent boil twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The principal method of manufacturing ethyl acetate is to react acetic acid with ethanol in the presence of a catalyst such as hydrochloric acid or sulfuric acid. An excess of ethanol is used thus converting all of the acetic acid to ethyl acetate and water. However, when the mixture is subjected to rectification, a ternary azeotrope boiling at 70.2° C. and comprising 82.16% ethyl acetate, 8.4% ethanol and 9% water comes off. Water is then added to this mixture which extracts the ethanol. However water is about 4% soluble in ethyl acetate and forms a minimum azeotrope with it. Thus both the ethanol and the ethyl acetate have to have the water removed as azeotropes by rectification. This reduces the yield per pass and requires additional recycling. Thus we see that conventional rectification is beset with problems of azeotrope formation and incomplete recovery due to recycling requirements. Extractive distillation is an attractive method of effecting the separation of ethyl acetate from ethanol and water if agents can be found that (1) will break the ethyl acetate-ethanol-water ternary azeotrope and (2) are easy to recover from the ethanol and water removed from the ethyl acetate.

Extractive distillation typically requires the addition of an equal amount to twice as much extractive agent as the ethyl acetate-ethanol-water on each plate in the rectification column. The extractive agent should be heated to about the same temperature as the plate into which it is introduced. Thus extractive distillation imposes an additional heat requirement on the column as well as somewhat larger plates. However this is usually less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with water otherwise it will form a two phase azeotrope with the water in the recovery column and some other method of separation will have to be employed.

The principal method of producing ethyl acetate is by the reaction of ethanol with acetic acid. This method produces water and so the separation of the ethyl acetate from the reaction mixture involves the formation of the ethyl acetate-ethanol-water ternary azeotrope.

OBJECTIVE OF THE INVENTION

The object of this invention is to provide a process or method of extractive distillation that will enhance the relative volatility of ethyl acetate from ethanol and water in their separation in a rectification column. It is a further object of this invention to identify suitable extractive distillation agents which will eliminate the ethyl acetate-ethanol-water ternary azeotrope and make possible the production of pure ethyl acetate by rectification. It is a further object of this invention to identify organic compounds which, in addition to the above constraints, are stable, can be separated from ethanol and water by rectification with relatively few plates and can be recycled to the extractive distillation column and reused with little decomposition.

SUMMARY OF THE INVENTION

The objects of this invention are provided by a process for separating ethyl acetate from ethanol and water which entails the use of certain oxygenated and/or nitrogenous organic compounds as the agent in extractive distillation.

DETAILED ELABORATION OF THE INVENTION

We have discovered that certain oxygenated and/or nitrogenous compounds, some individually but principally as mixtures, will effectively negate the ethyl acetate-ethanol-water ternary azeotrope and permit the separation of pure ethyl acetate by rectification when employed as the agent in extractive distillation. Table I lists the compounds, mixtures and approximate proportions that we found to be successful. Table II lists mixtures that we investigated and found to be relatively ineffective.

The compounds that are effective as extractive distillation agents when used alone are N,N-dimethylformamide (DMFA), dimethylsulfoxide (DMSO) and propylene glycol. The compounds which are effective when used in mixtures of two, three or four components are phenol, m-p-cresol, o-sec. butylphenol, o-tert. butylphenol, catechol, hydroquinone, resorcinol, 1-naphthol, 2-naphthol, acetophenone, ethyl acetoacetate, glycerine, dibutylphthalate, dioctylphthalate, diisooctylphthalate, diisodecylphthalate, ethylene glycol phenyl ether, 1,5-pentanediol, diethylene glycol, triethylene glycol, tetraethylene glycol, hexylene glycol, diethylene glycol diethyl ether, butoxypropanol, dipropylene glycol methyl ether, propylene glycol and dipropylene glycol. The relative volatility of the agents shown in Table I varies from a high of 2.95 for DMSO-glycerine to 1.29 for DMFA-butoxypropanol. Table II lists combinations of some of the same compounds presented in Table I which failed to give relative volatilities as high as 1.29. This indicates the importance of employing these compounds in the proper ratio and combination.

THE USEFULNESS OF THE INVENTION

The usefulness or utility of this invention can be demonstrated by referring to the data presented in Table I. All of the successful reagents show that ethyl acetate can be removed from its ternary azeotrope with ethanol and water by means of distillation in a rectification column and that the ease of separation as measured by the relative volatility is considerable. Without these extractive distillation agents, no change in the azeotrope composition will occur in the rectification column. The data also show that the most attractive agents will operate at a boilup rate high enough to make this a useful and attractive method of recovering high purity ethyl acetate from its ternary azeotrope with ethanol and water. The stability of the compounds used is such that complete recovery and recycle is obtainable by a simple distillation and the amount required for make-up is small.

TABLE I

Extractive Distillation Agents Which Are Effective In Separating Ethyl Acetate From Ethanol and Water.

| Compounds | Ratio | Relative Volatility |
|---|---|---|
| o-tert.Butylphenol, Resorcinol, Hydroquinone, DMFA | 1:1:1:1 | 1.37 |
| Phenol, o-sec.Butylphenol, DMFA, Ethylacetoacetate | 1:1:1:1 | 1.30 |
| Catechol, m-p-Cresol, Hydroquinone, DMFA | 1:1:1:1 | 1.36 |
| Hydroquinone, Resorcinol, m-p-Cresol, DMSO | 1:1:1:1 | 1.34 |
| Hydroquinone, Catechol, m-p-Cresol, DMSO | 1:1:1:1 | 1.30 |
| Hydroquinone, Catechol, Resorcinol, DMSO | 1:1:1:1 | 1.24 |
| 2-Naphthol, Catechol, DMFA | 1:1:2 | 1.59 |
| 2-Naphthol, Hydroquinone, DMFA | 1:1:2 | 1.38 |
| 1-Naphthol, Hydroquinone, DMFA | 1:1:2 | 1.50 |
| 1-Naphthol, Catechol, DMFA | 1:1:2 | 1.50 |
| 1-Naphthol, Resorcinol, DMFA | 1:1:2 | 1.52 |
| 1-Naphthol, Hydroquinone, DMFA | 1:1:2 | 1.74 |
| Catechol, Resorcinol, DMFA | 1:1:2 | 1.31 |
| o-sec.Butylphenol, o-tert.Butylphenol, DMSO | 1:1:1 | 1.34 |
| Hydroquinone, m-p-Cresol, DMSO | 1:1:1 | 1.36 |
| Catechol, m-p-Cresol, DMSO | 1:1:1 | 1.36 |
| Glycerine, DMSO, Diethylene glycol | 1:1:1 | 2.55 |
| Glycerine, DMSO, Dioctylphthalate | 1:1:1 | 2.44 |
| Glycerine, DMSO, Hexylene glycol | 1:1:1 | 2.10 |
| Glycerine, DMSO, Dibutylphthalate | 1:1:1 | 1.86 |
| Glycerine, DMSO, Ethylene glycol phenyl ether | 1:1:1 | 2.25 |
| Glycerine, DMSO, 1,5-Pentanediol | 1:1:1 | 2.45 |
| Glycerine, DMSO, Tetraethylene glycol | 1:1:1 | 2.40 |
| Glycerine, DMSO, Butoxypropanol | 1:1:1 | 2.38 |
| Glycerine, DMSO, Triethylene glycol | 1:1:1 | 2.50 |
| Glycerine, DMSO, Propylene Glycol | 1:1:1 | 2.90 |
| m-p-Cresol, DMFA | 1:1 | 1.30 |
| Phenol, DMFA | 1:1 | 1.36 |
| Resorcinol, DMSO | 1:1 | 1.84 |
| Hydroquinone, DMFA | 1:1 | 1.81 |
| o-tert.Butylphenol, DMSO | 1:1 | 1.60 |
| Resorcinol, DMFA | 1:1 | 1.51 |
| Hydroquinone, DMSO | 1:1 | 1.88 |
| DMSO, Diethylene glycol diethyl ether | 1:1 | 1.63 |
| DMSO, Ethylene glycol phenyl ether | 1:1 | 2.01 |
| DMFA, Ethylene glycol phenyl ether | 1:1 | 1.42 |
| DMSO, Butoxypropanol | 1:1 | 1.67 |
| DMFA, Butoxypropanol | 1:1 | 1.29 |
| DMSO, Diethylene glycol | 1:1 | 2.56 |
| DMFA, Diethylene glycol | 1:1 | 1.89 |
| DMSO, Diisooctylphthalate | 1:1 | 2.52 |
| DMSO, Dioctylphthalate | 1:1 | 2.37 |
| DMSO, Dipropylene glycol methyl ether | 1:1 | 1.85 |
| DMFA, Dipropylene glycol methyl ether | 1:1 | 1.45 |
| Diethylene glycol, Dioctylphthalate | 1:1 | 1.74 |
| Diethylene glycol, Diisooctylphthalate | 1:1 | 1.45 |
| DMSO, Diisodecylphthalate | 1:1 | 1.80 |
| DMSO, Dibutylphthalate | 1:1 | 1.80 |
| DMSO, Hexylene glycol | 1:1 | 2.32 |
| DMSO, Propylene glycol | 1:1 | 2.63 |
| DMSO, Glycerine | 1:1 | 2.95 |
| DMFA, Glycerine | 1:1 | 2.08 |
| Glycerine, Hexylene glycol | 1:1 | 2.25 |
| Glycerine, Diethylene glycol | 1:1 | 2.70 |
| DMSO, Dipropylene glycol | 1:1 | 1.88 |
| N,N—Dimethylformamide (DMFA) | 2 | 1.64 |
| Dimethylsulfoxide (DMSO) | 2 | 2.75 |
| Propylene glycol | 2 | 2.30 |
| Ethylene glycol | 2 | 2.76 |

TABLE II

Extractive Distillation Agents Which Are Relatively Ineffective.

| Compounds | Ratio | Relative Volatility |
|---|---|---|
| Hydroquinone, Catechol, o-sec.Butylphenol, DMFA | 1:1:1:1 | 1.03 |
| Hydroquinone, Catechol, o-tert.Butylphenol, DMFA | 1:1:1:1 | 1.06 |
| o-tert.Butylphenol, m-p-Cresol, Acetophenone, Ethylacetoacetate | 1:1:1:1 | 0.82 |
| Hydroquinone, Resorcinol, Ethylacetoacetate, DMFA | 1:1:1:1 | 1.21 |
| Hydroquinone, Phenol, Ethylacetoacetate, DMFA | 1:1:1:1 | 1.17 |
| 1-Naphthol, Resorcinol, Ethylacetoacetate, DMFA | 1:1:1:1 | 1.19 |
| 2-Naphthol, Resorcinol, Ethylacetoacetate, DMFA | 1:1:1:1 | 1.26 |
| m-p-Cresol, Acetophenone, Ethylacetoacetate | 1:1:1 | 1.05 |
| Phenol, o-sec.Butylphenol, DMFA | 1:1:1 | 0.92 |
| Phenol, Hydroquinone, Acetophenone | 1:1:1 | 1.04 |
| Phenol, Resorcinol, Acetophenone | 1:1:1 | 0.96 |
| Hydroquinone, Ethylacetoacetate | 1:1:1 | 1.28 |
| m-p-Cresol, o-tert.Butylphenol | 1:1 | 1.09 |
| Acetophenone, DMFA | 1:1 | 1.19 |
| DMFA, Diethylene glycol diethyl ether | 1:1 | 1.15 |
| Ethylene glycol phenyl ether, Butoxypropanol | 1:1 | 0.84 |
| DMFA, Diisooctylphthalate | 1:1 | 1.18 |
| DMFA, Dioctylphthalate | 1:1 | 1.18 |
| Glycerine | 2 | Insol. |

WORKING EXAMPLES

Example 1

The ethyl acetate-ethanol-water azeotrope is 82.6% ethyl acetate, 8.4% ethanol and 9.0% water. Fifty grams of the EtAc-EtOH-H$_2$O azeotrope and fifty grams of dimethylsulfoxide (DMSO) was charged to an Othmer type glass vapor-liquid equilibrium still and refluxed for eleven hours. Analysis of the vapor and liquid by gas chromatography gave vapor: 92.4% EtAc, 7.6% EtOH; a liquid of 80% EtAc, 20% EtOH. This indicates a relative volatility of 3.12. Ten grams of DMSO were added and refluxing continued for another twelve hours. Analysis indicated a vapor composition of 91.8% EtAc, 8.2% EtOH, a liquid of 82.6% EtAc, 17.4% EtOH which is a relative volatility of 2.39.

Example 2

Fifty grams of the EtAc-EtOH-H$_2$O azeotrope and fifty grams of N,N-dimethylformamide (DMFA) were charged to the vapor-liquid equilibrium still and refluxed for eleven hours. Analysis indicated a vapor composition of 93.2% EtAc, 6.8% EtOH, a liquid composition of 86.7% EtAc, 13.3% EtOH which is a relative volatility of 1.73. Ten grams of DMFA were added and refluxing continued for twelve hours. Analysis then indicated a vapor composition of 91.1% EtAc, 8.9% EtOH, a liquid composition of 86.9% EtAc, 13.1% EtOH which is a relative volatility of 1.55.

Example 3

Fifty grams of the EtAc-EtOH-H$_2$O azeotrope, 25 grams of m-p-cresol and 25 grams of DMFA were charged to the vapor-liquid equilibrium still and refluxed for eleven hours. Analysis indicated a vapor composition of 90.1% EtAc, 9.9% EtOH, a liquid composition of 87.7% EtAc, 12.3% EtOH which is a relative volatility of 1.27. Five grams of m-p-cresol and five grams of DMFA were added and refluxing continued for 13 hours. Analysis indicated a vapor composition of 91.0% EtAc, 9.0% EtOH, a liquid composition of 88.3% EtAc, 11.7% EtOH which is a relative volatility of 1.33.

Example 4

Fifty grams of the EtAc-EtOH-H$_2$O azeotrope, 17 grams of glycerine, 17 grams of DMSO and 17 grams of dioctylphthalate were charged to the vapor-liquid equilibrium still and refluxed for ten hours. Analysis indicated a vapor composition of 92.1% EtAc, 7.9% EtOH, a liquid composition of 81.6% EtAc, 18.4% EtOH which is a relative volatility of 2.64. Three grams each of glycerine, DMSO and dioctylphthalate were added and refluxing continued for eleven hours. Analysis indicated a vapor composition of 92.0% EtAc, 8% EtOH and a liquid composition of 83.7% EtAc, 16.3% EtOH which is a relative volatility of 2.25.

Example 5

Fifty grams of the EtAc-EtOH-H$_2$O azeotrope, 12.5 grams of hydroquinone, 12.5 grams of catechol, 12.5 grams of resorcinol and 12.5 grams of DMSO were charged to the vapor-liquid equilibrium still and refuxed for eleven hours. Analysis indicated a vapor composition of 90.3% EtAc, 9.7% EtOH and a liquid composition of 87.8% EtAc, 12.2% EtOH which is a relative volatility of 1.28. 2.5 grams of each agent was added and refluxing continued for another twelve hours. Analysis indicated a vapor composition of 90.2% EtAc, 9.8% EtOH and a liquid composition of 88.5% EtAc, 11.5% EtOH which is a relative volatility of 1.20.

These examples show how an initial evaluation of potential extractive distillation agents can be accomplished for single, binary, ternary and quaternary agents. The final step in this invention is to determine the efficacy of these agents in a rectification column. When a mixture of ethyl acetate-ethanol-water is charged to a rectification column, we encounter a system involving three compounds and four azeotropes. Their boiling points and compositions are shown in Table III.

TABLE III

Azeotropes in the Ethyl acetate-Ethanol-Water System.

| | B.P, °C. | EtOH | EtAc | H$_2$O |
|---|---|---|---|---|
| Ethanol | 78.3 | | | |
| Ethyl acetate | 77.1 | | | |
| Water | 100 | | | |
| Ethanol-Water | 78.2 | 95.4 | | 4.6 |
| Ethyl acetate-Water | 70.4 | | 91.9 | 8.1 2-phase |
| Ethanol-Ethyl acetate | 71.8 | 31 | 69 | |
| Ethanol-Ethyl acetate-Water | 70.2 | 8.4 | 82.6 | 9.0 |

In conventional rectification, the lowest boiling component in Table III will boil off first, namely the ethyl acetate-ethanol-water azeotrope at 70.2° C. However when the proper extractive distillation agent is employed, the ternary azeotrope and all three binary azeotropes are suppressed and pure ethyl acetate comes off as overhead. The following examples will elaborate.

Example 6

A column consisting of six 1½ inch diameter glass perforated plates equipped with a vacuum jacket was employed. The column was fitted with a Corad constant reflux ratio distilling head. Between the Corad head and the top of the column, a feed line from a constant flow bellows pump was introduced. The stillpot was equipped with a sampling tube. The column was calibrated with a test mixture of ethylbenzene and p-xylene, which mixture possesses a relative volatility of 1.06. At total reflux, the column calibrated 4.5 theoretical plates. A run was then made with a 500 gram charge to the stillpot comprising 43.2% ethyl acetate, 49.6% ethanol, 7.2% water. The extractive agent was fed to the bellows pump from a steam jacketed calibrated reservoir which maintained it at about 95° C.

The pump was started and a rate of introduction of the extractive agent at the top of the column maintained at about twice the boilup rate as determined in the Corad head. The extractive agent in this example consisted of one part by weight of glycerine plus one part of dimethylsulfoxide (DMSO). The column was operated at total reflux for about 1½ hours with sampling after one hour and after 1½ hours. The following data was obtained.

| | Overhead Composition | | Stillpot Composition | | Relative |
|---|---|---|---|---|---|
| Time, hrs. | % EtAc | % EtOH | % EtAc | % EtOH | Volatility |
| 1 | 98.82 | 1.18 | 44.44 | 55.56 | 2.81 |
| 1.5 | 98.79 | 1.21 | 39.6 | 60.4 | 2.92 |

It will be noted that equilibrium was attained after about an hour with the relative volatility becoming almost constant. Without the extractive agent the overhead would have approached 82.6% ethyl acetate, the ternary azeotrope composition. With the extractive agent, the ternary appears to be completely absent and the ethyl acetate concentration in the overhead approaches 100%.

Example 7

The glycerine and DMSO from Example 6 was separated from the ethyl acetate, ethanol and water in a distilling flask and re-used in the same manner as Example 6. This time the following data was obtained.

| Time, hrs. | Overhead Composition | | Stillpot Composition | | Relative Volatility |
|---|---|---|---|---|---|
| | % EtAc | % EtOH | % EtAc | % EtOH | |
| 1 | 99.09 | 0.91 | 43.6 | 56.4 | 3.00 |
| 1.5 | 98.95 | 1.05 | 41.9 | 58.1 | 2.95 |

This example demonstrates the ability of the extractive distillation agent to be recovered and re-used with no loss in efficiency of separation.

Example 8

Four hundred grams of the ethyl acetate-ethanol-water azeotrope was charged to the stillpot of the apparatus described in Example 6. The extractive agent was DMSO, the boilup rate was 12 ml/min. and the DMSO feed rate was 24 ml/min. The column was operated at total reflux for 1.5 hours and the following data was obtained.

| Time, hrs. | Overhead Composition | | Stillpot Composition | | Relative Volatility |
|---|---|---|---|---|---|
| | % EtAc | % EtOH | % EtAc | % EtOH | |
| 1 | 99.82 | 0.18 | 86.52 | 13.48 | 2.69 |
| 1.5 | 99.83 | 0.17 | 85.76 | 14.24 | 2.77 |

This example demonstrates the ability of the extractive distillation agent to start with the ethyl acetate-ethanol-water ternary azeotrope as feed and produce high purity ethyl acetate.

In the manner described in Examples 6, 7 and 8, data was gathered on several extractive distillation agents and the results summarized in Table IV. In each case, operation was carried out for 1.5 hours at total reflux and sampling done at one and 1.5 hours. The extractive agent was separated from the ethyl acetate-ethanol-water mixture in a distilling flask and the run repeated with the recovered agent, this to demonstrate the ability of these agents to be recovered and recycled without loss of efficiency.

TABLE IV

Relative Volatilities Obtained With a 4.5 Theoretical Plate Column.

| Extractive Agents | Relative Volatilities | | | |
|---|---|---|---|---|
| | Fresh Charge | | Re-used Charge | |
| | 1 hr. | 1.5 hrs. | 1 hr. | 1.5 hrs. |
| DMSO | 2.69 | 2.77 | 2.76 | 2.63 |
| DMFA | 1.62 | 1.78 | 1.49 | 1.71 |
| Propylene glycol | 2.76 | 2.99 | 2.54 | 2.98 |
| Propylene glycol, DMSO | 2.61 | 2.89 | 2.55 | 2.61 |
| o-tert.Butylphenol, DMSO | 1.61 | 1.60 | 1.47 | 1.56 |
| Diethylene glycol, DMSO | 2.69 | 2.91 | 2.52 | 2.73 |
| Diisooctylphthalate, DMSO | 2.60 | 2.62 | 2.25 | 2.47 |
| Diisodecylphthalate, DMSO | 1.96 | 1.93 | 1.65 | 1.63 |
| Glycerine, DMSO | 2.81 | 2.92 | 3.03 | 2.95 |
| o-tert.Butylphenol, DMFA | 1.29 | 1.31 | 1.34 | 1.29 |

We have shown by the use of the proper compound or combination of compounds as agents, ethyl acetate can be effectively removed and recovered from its mixture or ternary azeotrope with ethanol and water.

The nature of the present invention having been described, what we wish to claim as new and useful and secure by Letters Patent is:

1. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes dimethylsulfoxide.

2. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes N,N-dimethylformamide.

3. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes ethylene glycol.

4. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes propylene glycol.

5. The method of claim 1 in which the extractive agent comprises a mixture of dimethylsulfoxide and one or more of the following: catechol, hydroquinone, resorcinol, phenol, m-p-cresol, o-sec. butylphenol, o-tert. butylphenol, glycerine, ethylene glycol, diethylene glycol, triethylene glycol, tetraethylene glycol, propylene glycol, dipropylene glycol, hexylene glycol, dibutylphthalate, dioctylphthalate, diisooctylphthalate, diisodecylphthalate, ethylene glycol phenyl ether, 1,5-pentanediol, butoxypropanol, diethylene glycol diethyl ether, dipropylene glycol methyl ether.

6. The method of claim 2 in which the extractive agent comprises a mixture of N,N-dimethylformamide and one or more of the following: catechol, hydroquinone, resorcinol, phenol, o-sec. butylphenol, o-tert. butylphenol, m-p-cresol, 1-naphthol, 2-naphthol, ethylacetoacetate, ethylene glycol phenyl ether, butoxypropanol, diethylene glycol, glycerine, dipropylene glycol methyl ether, acetophenone, diethylene glycol diethyl ether, dioctylphthalate, diisooctylphthalate.

7. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes a mixture of diethylene glycol and dioctylphthalate.

8. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes a mixture of diethylene glycol and diisooctylphthalate.

9. A method for recovering ethyl acetate from a mixture of ethyl acetate, ethanol and water which comprises distilling a mixture of ethyl acetate, ethanol and water in a rectification column in the presence of an effective amount of an extractive agent, recovering essentially pure ethyl acetate as overhead product and obtaining the extractive agent, ethanol and water from the stillpot or reboiler, the extractive agent includes a mixture of hydroquinone and ethylacetoacetate.

* * * * *